United States Patent [19]

Sayles

[11] 4,150,057
[45] Apr. 17, 1979

[54] METHOD FOR PREPARATION OF A CARBORANYL BURNING RATE ACCELERATOR PRECURSOR

[75] Inventor: David C. Sayles, Huntsville, Ala.

[73] Assignee: The United States of America as represented by the Secretary of the Army, Washington, D.C.

[21] Appl. No.: 891,253

[22] Filed: Mar. 29, 1978

[51] Int. Cl.$^2$ .............................................. C07F 5/02
[52] U.S. Cl. .............................................. 260/606.5 B
[58] Field of Search .................................. 260/606.5 B

[56] References Cited

U.S. PATENT DOCUMENTS

| | | | |
|---|---|---|---|
| 3,154,561 | 10/1964 | Muetterties | 260/606.5 B X |
| 3,296,260 | 1/1967 | Knoth | 260/606.5 B X |
| 3,489,812 | 1/1970 | Marshall et al. | 260/606.5 B |

Primary Examiner—Helen M. S. Sneed
Attorney, Agent, or Firm—William G. Gapcynski; Werten F. W. Bellamy; Jack W. Voight

[57] ABSTRACT

Disclosed is a method of synthesis and the compound synthesized $B_{10}H_{12}[(CH_3)_2S]_2$. The method employs the starting compound $(R_4N)_2B_{10}H_{10}$, as a source of the ten-boron ion (e.g., $B_{10}H_{10}{}^{-2}$), in which the starting compound, wherein R equals an alkyl with the formula $C_nH_{2n+1}$ and wherein n equals 2, 3, or 4, is converted to $Li_2B_{10}H_{10}$ by ion-exchange. The $Li_2B_{10}H_{10}$ is reacted with HCl in $(CH_3)_2S$ solution to produce the compound $B_{10}H_{12}[(CH_3)_2S]_2$, a precursor compound for synthesizing carboranyl burning rate accelerators. The precursor compound is reacted with propargyl propionate if the interest is to synthesize carboranylmethyl propionate; 1-octyne to synthesize n-hexylcarborane; or propargyl ethyl sulfide or propargyl propyl sulfide to synthesize carboranylmethyl ethyl sulfide or carboranylmethyl propyl sulfide, respectively.

2 Claims, No Drawings

METHOD FOR PREPARATION OF A CARBORANYL BURNING RATE ACCELERATOR PRECURSOR

DEDICATORY CLAUSE

The invention described herein may be manufactured, used, and licensed by or for the Government for governmental purposes without the payment to me of any royalties thereon.

CROSS-REFERENCE TO RELATED APPLICATION

The method of preparation for the starting compound and the starting compound for preparing the carboranyl burning rate accelerator precursor of this invention are disclosed in my concurrently filed patent application, Ser. No. 891,254, filed Mar. 29, 1978, titled: "Precursor for Carboranyl Burning Rate Accelerator, Method of Synthesis".

BACKGROUND OF THE INVENTION

Carboranyl burning rate accelerators, also referred to as carborane catalysts, have been of interest in the preparation of ultrahigh-burning-rate propellants of the composite-modified, double-base, composite (the latter having terminal functionality of carboxyl and hydroxyl), or difluoroamino-plasticized, ethyl acrylate-acrylic acid-based types.

The presently-used procedure for the synthesis of currently useful carborane catalyst include:

(1) Preparation of diborane;
(2) Thermolytic conversion of diborane into decaborane; and,
(3) Reaction of decaborane with a substituted alkyne to yield the carboranyl burning-rate accelerator.

The severe limitations of the presently-used method are low conversions, low yields, and the resulting extremely high costs of the carboranyl chemicals. In view of the high costs and other relevant limitations, the need for a better synthesis method is much desired.

A particular route for the synthesis of diborane via the reduction method of boric oxide (or boric acid or metal borate) in the presence of aluminum powder, anhydrous aluminum chloride, and sodium chloride has been considered for the source of diborane for conversion to decaborane which is then reacted with a selected alkynyl alkanate or alkyne to form a variety of carboranyl burning rate catalysts. Since this route for the synthesis of diborane requires high temperature and high pressure operation it imposes disadvantages and limitations which encourage the development of a less involved process for producing a precursor decaborane derivative compound which can subsequently be converted to the carboranyl burning rate catalysts.

Therefore, an object of this invention is to provide a better synthesis method for producing precursor decaborane derivatives which can be readily converted to a precursor compound for carboranyl burning rate catalysts which have a proven performance record.

A further object of this invention is to provide a synthesis method for producing a precursor compound for preparing a variety of carboranyl catalysts by the selection and addition of a second reactant to yield the final desired carboranyl catalyst.

Still, a further object of this invention is to provide a method of synthesis for producing a precursor compound which does not require the production of diborane and decaborane intermediates that are highly toxic and spontaneously inflammable in air at high concentrations.

SUMMARY OF THE INVENTION

The starting compound for preparing $Li_2B_{10}H_{10}$ is a compound selected from the compounds of the formula $(R_4N)_2B_{10}H_{10}$, wherein R equals an alkyl with the formula $C_nH_{2n+1}$ and wherein n equals 2, 3, or 4. The starting compound is converted to dilithiodecaborane-10 by cation exchange. The dilithiodecaborane-10 is reacted with hydrogen chloride and dimethyl sulfide to form $B_{10}H_{12}[(CH_3)_2S]_2$, a favored precursor for these carboranyl burning rate accelerators. Chemical reaction equation 1 represents the cation exchange reaction which is accomplished with a yield of about 95%.

Equation (1):
$(R_4N)_2B_{10}H_{10} + 2LiX \rightarrow Li_2B_{10}H_{10} + 2R_4NX$, wherein R equals an alkyl of the formula $C_nH_{2n+1}$ and n equals 2, 3, or 4, and wherein X is a halogen selected from chlorine, bromine or iodine.

Chemical reaction equation 2 represents the reaction step at 25° C. with HCl gas and excess dimethyl sulfide as solvent to produce the precursor compound of this invention in a yield of about 85%.

Equation (2):
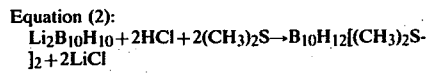
$Li_2B_{10}H_{10} + 2HCl + 2(CH_3)_2S \rightarrow B_{10}H_{12}[(CH_3)_2S]_2 + 2LiCl$ Oxygen and moisture are excluded by using a nitrogen gas purge.

DESCRIPTION OF THE PREFERRED EMBODIMENT

The precursor compound of this invention, $B_{10}H_{12}[(CH_3)_2S]_2$, is prepared by way of the cation exchange, chemical reaction equation No. 3 and the subsequent reaction as shown by chemical reaction equation No. 4.

Equation (3):
$(R_4N)_2B_{10}H_{10} + 2LiCl \rightarrow Li_2B_{10}H_{10} + 2R_4NCl$ (R is as earlier defined).

The $Li_2B_{10}H_{10}$ must be thoroughly dried before use in reaction chemical equation 4. A stream of dry hydrogen chloride can be used as the source of HCl in equation 4.

Equation (4):
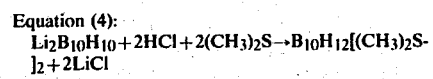
$Li_2B_{10}H_{10} + 2HCl + 2(CH_3)_2S \rightarrow B_{10}H_{12}[(CH_3)_2S]_2 + 2LiCl$ The method of synthesis for the compound which serves as the starting compound for the method of this invention is summarized below (Equations 5 and 6) along with yields achieved for the overall step of reaction.

Preparation of $R_4NBH_4$

Equation (5):
$NaBH_4 + R_4NX \rightarrow R_4NBH_4 (70-80\%) + NaX$ wherein R equals an alkyl of the formula $C_nH_{2n+1}$ and n equals 2, 3, or 4, and wherein X is a halogen selected from chlorine, bromine, and iodine.

Pyrolysis of $R_4NBH_4$ (where R equals $C_2H_5$, i.e. Et)

Equation (6):
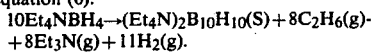
$$10Et_4NBH_4 \rightarrow (Et_4N)_2B_{10}H_{10}(S) + 8C_2H_6(g) + 8Et_3N(g) + 11H_2(g).$$

85% (Starting Compound).

The results of ion exchange in Equation 5 and pyrolysis in Equation 6 converts $BH_4^-$ to $B_{10}H_{10}^{-2}$. The starting compound is converted to the $Li^+$ form by ion exchange. The $B_{10}H_{10}^{-2}$ of the dilithiodecaborane-10 reacts with hydrogen chloride and dimethyl sulfide to form $B_{10}H_{12}[(CH_3)_2S]_2$, a favored NHC precursor.

The detailed preparative procedure for $(Et_4N)_2B_{10}H_{10}$, a compound of the group $(R_4N)_2B_{10}H_{10}$, includes (1) preparation of tetraethylammonium tetrahydridoborane by conversion of a quaternary ammonium halide and sodium borohydride through use of sodium-form of a cation exchange resin column, and (2) the pyrolysis of this compound to yield $(Et_4N)_2B_{10}H_{10}$ as described below. Also presented below is the preparation of quaternary ammonium iodides since they are key starting compounds. The equivalent compounds, e.g., the bromides and chlorides, can be prepared by modifying the process. The quaternary bromides and chlorides in the equivalent amounts can be used in the cation exchange procedure.

1. Preparation of Tetraethylammonium Tetrahydridoborane

Two measuring burets (100 or 250 cc) are modified to function as ion exchange columns by placing a glass wool plug at their bottoms to retain the cation exchange resin, and then by filling them with water. A cation exchange resin ($Na^+$ form) (20–50 mesh) (100 ml) is added gradually through the top of each column while water is withdrawn from the bottom of the column. The resin is converted to the tetraethylammonium form by flowing an excess of an aqueous solution of $Et_4NI$ for each 100 ml. of wet resin. (Note: If the equivalent compound $Et_4NCl$ is used, about 29 grams should be used. Also, if the equivalent compound $Et_4NBr$ is used about 36 grams per 100 ml. of wet resin should be used.) Each column is then washed with several volumes of aqueous isopropanol (60% by volume). Sodium borohydride (up to a maximum of 6 grams $NaBH_4$ per 100 ml of wet resin in the first column) is dissolved in the minimum volume of 60% aqueous isopropanol at room temperature, and passed rapidly (2–5 ml/min) through the first column. The column is eluted with 60% aqueous isopropanol until drops of effluent no longer reduces $Ag^+$ to metallic silver. The effluent is then passed through the second column in similar fashion. The effluent of the second column is placed in a large porcelain evaporating dish, and warmed (to below 40° C.) in a well-ventilated fume hood. When the volume is reduced to about 100 ml., the remaining liquid is removed under reduced pressure. The solid $(C_2H_5)_4NBH_4$ is dried at 40° C. under reduced pressure.

2. Pyrolysis of Tetraethylammonium Tetrahydridoborane

A stainless steel, high pressure Hoke cylinder, of 150 ml. capacity, and fitted with a 150 ml, single-ended sampling device is charged with tetraalkylammonium tetrahydridoborane (7 grams, 0.05 moles). The stoichiometry is depicted in the following chemical equation:

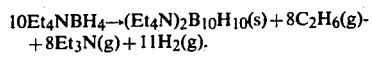
$$10Et_4NBH_4 \rightarrow (Et_4N)_2B_{10}H_{10}(s) + 8C_2H_6(g) + 8Et_3N(g) + 11H_2(g).$$

The cylinder is fitted with a Hoke valve, of 4100 series stainless steel, and evacuated on a vacuum line. The valve is closed, and the cylinder immersed in an oil bath maintained at room temperature. The oil bath is then heated to 185° C., and this temperature held for 18 hours. The bomb is allowed to cool, and it is vented, and the valve removed. Acetonitrile (50 ml) is added, and swirled to dissolve any unreacted starting material and other soluble impurities. The acetonitrile is decanted from the settled solids and discarded. Water (50 ml) is added to the cylinder and shaken vigorously. The cylinder is then inverted over a 250 ml beaker. This procedure is repeated using a second portion of water (50 ml). A third portion of water (50 ml) is added to the cylinder, and the cylinder is heated to 100° C. for 15 minutes; this portion is then added to the previous two portions. The combined water solutions are heated to boiling and filtered. The filtrate is concentrated to a thin syrup and the $(Et_4N)_2B_{10}H_{10}$ is allowed to undergo crystallization.

The crystallized $(Et_4N)_2B_{10}H_{10}$ is a source of ten-boron ion $B_{10}H_{10}^{-2}$ which can be treated with acid and dimethyl sulfide to form a preferred precursor which is reacted with 1-octyne to give NHC.

The crystallized compound is readily converted to dilithiodecaborane-10, as shown in Equation 3, as follows:

Preparation of Dilithiodecaborane-10

A measuring buret, of 250 ml capacity, is filled with Dowex 50 X8 resin (Na form) (200 ml). The resin is converted to the $Li^+$ form by treatment with lithium chloride (15g) in water (100 ml). The resin is washed with water until no chloride ion is detected. $(Et_4N)_2B_{10}H_{10}$ (30g) is then dissolved in water, and passed through the column at a rate of about 1 ml per minute. The product $(Li_2B_{10}H_{10})$ is eluted with pure water until testing of effluent drops with $Ag^+$ shows no further formation of the $B_{10}H_{10}^{-2}$ ion which would form a yellow-brown solid. The effluent is then concentrated by boiling off the water and finally dried at 100° under reduced pressure (~0.05 mm Hg). Because $Li_2B_{10}H_{10}$ is hygroscopic, it must be stored in a desiccator, or thoroughly dried immediately before use.

Dilithiodecaborane-10 is further reacted to produce bis(dimethyl sulfide)decaborane-12, the common precursor compound for producing carboranyl burning rate accelerators. The preparation of bis(dimethyl sulfide)decaborane-12 is accomplished as follows:

Preparation of Bis(dimethyl sulfide) Decaborane-12

A filter flask of 50 ml capacity is equipped with magnetic stirring bar and is purged with dry nitrogen gas. $Li_2B_{10}H_{10}$ (1g) is placed in the flask, and it is fitted with a 2-hole rubber stopper. The $N_2$ purge is continued but the flow rate is reduced to just maintain a positive pressure. Dimethyl sulfide (15 ml) is added through the stopper. A stream of dry hydrogen chloride is bubbled into the dimethyl sulfide with stirring until the solid $Li_2B_{10}H_{10}$ is dissolved. The apparatus is then connected to a water aspirator and the HCl and excess $(CH_3)_2S$ are pumped off. The product is recrystallized from dimethyl sulfide by dilution with pentane.

The following reaction equations represent the steps of producing n-hexylcarborane by the new route as disclosed by this invention. The percent yields obtained is also shown to the right of each equation for the product produced.

| Product | Yield |
|---|---|
| 1. $Et_4NBr$ $Et_3N + EtBr \rightarrow Et_4NBr$ | 95% |
| 2. $Et_4NBH_4$ $Et_4NBr + NaBH_4 \rightarrow Et_4NBH_4 + NaBr$ | 95% |
| 3. $(Et_4N)_2B_{10}H_{10}$ $10\ Et_4NBH_4 \rightarrow (Et_4N)_2B_{10}H_{10} + 8\ Et_3N + 8\ C_2H_6 + 11\ H_2$ | 98% |
| 4. $Li_2B_{10}H_{10}$ $(Et_4N)_2B_{10}H_{10} + 2\ LiCl \rightarrow Li_2B_{10}H_{10} + 2\ Et_4NCl$ | 95% |
| 5. $B_{10}H_{12}[(CH_3)_2S]_2$ $Li_2B_{10}H_{10} + 2\ HCl + 2(CH_3)_2S \rightarrow b_{10}H_{12}[(CH_3)_2S]_2 + 2\ LiCl$ | 85% |
| 6. $C_2B_{10}H_{10}(C_6H_{13})$(NHC, n-Hexylcarborane) $B_{10}H_{12}[(CH_3)_2S] + 1.5\ octyne \rightarrow C_2B_{10}H_{10}(C_6H_{13}) + (CH_3)_2S$ | 40% |

The high yields and the fact that many of the reactant media are recoverable for recycling renders the above route attractive overall in terms of effectiveness, although the yield of NHC by the octyne route is only 40%. Another route described below offers a high yield of NHC.

The raw materials cost analysis for the formation of NHC from $B_{10}H_{12}[(CH_3)_2S]_2$ utilizing propargyl bromide shows a large cost improvement. This process is outlined by equations 7, 8, and 9 as follows:

| Product | Yield |
|---|---|
| 7. $B_{10}H_{12}[(CH_3)_2S]_2 + HC\equiv CCH_2Br \rightarrow B_{10}H_{10}(C_3H_3Br)$ | 90% |
| 8. $B_{10}H_{10}C_3H_3Br + Mg \rightarrow B_{10}H_{10}C_3H_3MgBr$ | 95% |
| 9. $B_{10}H_{10}C_3H_3MgBr + Pentyl\ bromide \rightarrow NHC$ | 80% |

The crystallized compound, bis(dimethyl sulfide)-decaborane-12, is reacted with 1-octyne to yield a product identified as n-hexylcarborane. This reaction chemistry between a ligand and octyne or other acetylenic compounds to form n-alkylcarborane is well established in the art. This serves to characterize the structure of the precursor compound. The steps of preparation along with the reaction with octyne to yield n-hexylcarborane confirms the precursor compound's structure.

The usefulness of n-hexylcarborane and other carboranyl burning rate accelerators in propellant formulations is also well established in the art. The benefits and usefulness of the improved process for producing precursors for carboranyl burning rate accelerators, as disclosed by this invention, is apparent when the process steps are compared with process steps of alternate routes to producing carboranyl burning rate accelerators. The process of this invention is only limited by the production size quantities, by the size of ion exchange systems employed and the related equipment for pyrolyzing, extraction, and purification of the product produced. Ion exchange resin columns of large capacity have been employed in many industrial applications.

I. Preparation of Quaternary Ammonium Iodides

A general procedure is followed in which 20g (0.274 moles) of the appropriate butylamine is mixed with 150 ml of absolute ethanol; 37.8g (0.411 moles) of solid potassium carbonate is added to the solution in a 500 ml round bottom flask. The reaction is stirred magnetically, and a water cooled condenser is used. Methyl iodide (51.2 ml, 0.822 moles) or ethyl iodide (66.4 ml, 0.822 moles) is added in portions through the top of the condenser. Vigorous exotherms are observed on $CH_3I$ addition; milder heating occured with $C_2H_5I$, which could be added in three portions. After addition of alkyl iodide is complete, the reaction is refluxed overnight.

When n-butyl- or sec-butylamines are used, the reaction mixture is filtered warm and concentrated to a thin syrup in a rotary evaporator. The solution is decanted from a small amount of KI crystals, and chilled to crystallize the butyltrimethyl- or butyltriethylammonium iodide. Second crops are obtained by washing the filtered KI with 100 ml of absolute ethanol, combining with the supernatant liquid remaining from the first crop, then concentrating and crystallizing as previously. Yields typically are 70–80%, after recrystallization from water.

The quaternary t-butylammonium salts are found in the solid along with much solid KI. The filtered solids are dissolved in a minimum amount of boiling water and cooled to precipitate the quaternary t-butylammonium iodide. The filtered product is then recrystallized from water. Yields are somewhat lower than for the n-butyl and sec-butyl salts.

Analyses of the products for $I^-$ are given in Table I. Proton nmr results were also satisfactory, in that $^{14}N$ splitting characteristic of quaternary nitrogen was readily visible.

A series of tetraalkylammonium iodides can be prepared from monoalkyl amines and ethyl or methyl iodide. The iodides are converted to tetrahydridoborates by ion-exchange. The quaternary ammonium ions are placed on a cation exchange resin and then eluted with sodium borohydride in 3:2 isopropyl alcohol-water. Equation 5 illustrates the preparation of tetrahydridoborates with an overall yield of 70–80%.

The tetraalkylammonium borohydrides are pyrolyzed under various conditions to obtain $B_{10}H_{10}^{-2}$ ion. Increasing length and branching of the alkyl chains results in higher $B_{10}H_{10}^{-2}$ yields — the initiation temperature of pyrolysis decreased in the same order. Methyl groups are the least easily pyrolyzed and give the lowest yields of $B_{10}H_{10}^{-2}$.

TABLE I

| Iodide Analysis of Quaternary Salts | | |
|---|---|---|
| Compound | Calc $I^-$ | Found $I^-$ |
| n-butyltriethyl | 44.6% | 44.3, 44.6 |
| sec-butyltriethyl | 44.6 | 46.6, 46.6 |
| t-butyltriethyl | 44.6 | 43.6, 43.8 |
| n-butyltrimethyl | 52.3 | 52.2, 52.5 |
| sec-butyltrimethyl | 52.3 | 52.1, 52.0 |
| t-butyltrimethyl | 52.3 | 51.2, 52.6 |
| ethyltrimethyl | 59.0 | 57.7, 57.9 |

The preparation of the equivalent quaternary ammonium compounds, e.g., the bromides and chlorides, can be prepared by substituting the appropriate reactants in the above described procedures.

Special Preparative Procedures

Dowex 50-X8, a sodium-form of a cation exchange resin, is converted to the tetraalkylammonium form by treatment with the appropriate quaternary iodide in water. The column is washed with water until $Ag^+$ no longer detects the presence $I^-$ by the formation of AgI as a precipitate. In order to insure complete exchange in the shortest possible time, as many as three columns of resin are made ready for a single exchange reaction by flushing with 60/40 isopropyl alcohol/water. The $NaBH_4$ solution is prepared by saturating 60/40 isopropyl alcohol/$H_2O$ with $NaBH_4$; this solution is then passed (~5ml/min) successively through the three quaternary ammonium Dowex 50-X8 columns. The eluent is concentrated to a syrup in a large evaporating dish warmed by a hot plate. Evaporation is speeded by placing the evaporating dish in the mouth of a fume hood. The syrup is transferred to a vacuum line and dried. The final residues of water are removed by exhausting at 40° C. under full dynamic vacuum.

Since the pyrolysis of quaternary ammonium borohydrides is a key step in the formation of the starting compound of this invention, considerable evaluations were made to determine the preferred conditions for maximizing yield of product. These evaluations are described below along with the analytical data presented in Tables II–VI.

II. Pyrolysis of Quaternary Ammonium Borohydrides under Various Conditions

A. In Glass Under Vacuum

Table II shows that long times are needed to produce $B_{10}H_{10}^{-2}$ in an all-glass apparatus — even then, triethylaminoborane is a main product. This Table verifies the long times and poor yields encountered by others in attempted $B_{10}H_{10}^{-2}$ preparations in glass apparatus.

TABLE II

| $BH_4^-$ Pyrolyses in Glass Under Vacuum[A] | | | | | | |
|---|---|---|---|---|---|---|
| Compound Pyrolysed | Products[B] | | | | | |
| | $B_{10}H_{10}^{-2}$ | $B_{11}H_{14}^{-1}$ | $R_3NBH_3$ | $R_3N$ | RH | $H_2$ |
| $(C_2H_5)_4N^+BH_4^-$ (0.0410 mole) | 0.0025[C] (61.0%) | 0.00053[C] (14.2%) | 0.0100[C] (24.4%) | 0.0254[C] | 0.0360 | n.m.* |
| $(C_2H_5)_4N^+BH_4^-$ (0.0690 mole) | 0.0034[D] (49.3%) | 0.0009[D] (14.3%) | 0.0250[D] (36.2%) | 0.0352[D] | 0.0610 | n.m. |
| $(C_2H_5)_4N^+BH_4^-$ (0.0690 mole) | 0.0010[E] (14.5%) | 0[E] | 0.0370[E] (53.6%) | 0.0096 | 0.0466 | n.m. |

[A]500 cc Sublimation Apparatus
[B]Moles (yield based on $BH_4$ charged)
[C]At 155° C. for 50 hours.
[D]At 220° for 0.25 hours and at 185° for 28 hours.
[E]At 185° for 16 hours. Unreacted $Et_2N^+BH_4$ (0.0200 mole) was recovered.
*not measured

B. Pyrolysis in Glass under Pressure

Table III shows that little increse in $B_{10}H_{10}^{-2}$ yield occurs under autogenous pressure. Aminoboranes are principal products. The presence of $B_3H_8^-$ ion in one run suggests that this ion is an intermediate in $B_{10}H_{10}^{-2}$ formation, as does its further reaction with $BH_4^-$ to give a high yield of $B_{10}H_{10}^{-2}$.

TABLE III

| Pyrolysis in Sealed Glass at Autogenous Pressure[A] | | | | | | |
|---|---|---|---|---|---|---|
| Compounds(s) Pyrolysed | Products[B] | | | | | |
| | $B_{10}H_{10}^{2-}$ | $R_4N^+B_3H_8^-$ | $R_3NBH_3$ | $R_3N$ | RH | $H_2$ |
| $(C_2H_5)_4N^+BH_4^-$ (0.0410 mole) | 0[C] | 0.0073 (71.2%) | 0.0113 | 0.0200 | 0.0305 | n.m. |
| $(C_2H_5)_4N^+b_3H_8^-$[C] (0.0073 mole) | 0.0022 (54.6%) | 0 | 0 | 0.0029 | 0.0028 | n.m. |
| $(CH_3)_4N^+BH_4^-$ (0.045 mole) | 0.0002 (4.4%) | 0 | 0.0411 (91.3%) | 0.0024 | n.m. | n.m. |
| $(CH_3)_3(C_2H_5)N^+BH_4^-$ (0.0582 mole) | 0.0019 (32.8%) | 0 | 0.0384 (65.9%) | 0.0153 | 0.0150 | n.m. |
| $(C_2H_5)_4N^+BH_4^-$ (0.0300 mole) + $(C_2H_5)_3NBH_3$ (0.1260 mole) | 0.0029 (96.7%) | 0 | 0.1304 (103.5%) | 0.0230 | n.m. | n.m. |

(A) 150 cc Sealed glass bomb 190° C, 20 hours.
[B]Moles (yield based on reactant charged).
[C]The further pyrolyses of the product obtained during the reaction.
[D]Yield based on $BH_4^-$ charged.
[E]Yield based on $Et_3NBH_3$ charged.
n.m. not measured since the bond was opened in air after cooling.

TABLE IV

| $BH_4^-$ Pyrolysis in Glass at 1-Atmospheric Pressure[A] (Stainless Steel Catalyst Added) | | | | | | |
|---|---|---|---|---|---|---|
| Compound Pyrolysed | $B_{10}H_{10}^{2-}$ | $B_{11}H_{14}^-$ | $Et_3NBH_3$ | $Et_3N$ | $C_2H_6$ | $H_2$ |
| $(C_2H_5)_4N^+BH_4^-$ (0.0828 mol) | 0.0049 (59.0%) | 0.0008 (10.7%) | n.m.[C] | n.m. | n.m. | n.m. |

[A]500 cc three necked glass apparatus, at 185° C., 30 hours under a stream of Dry $N_2$.
[B]Moles (yield based on $BH_4$ charged).
[C]Not measured; expelled through a stream of $N_2$.

C. Pyrolysis in glass with steel catalyst added.

Table IV shows the rather poor yield (~60%) of $B_{10}H_{10}^{-2}$ ion found when the pyrolysis is carried out at 1 atmosphere. The lower yield (at 1 atmosphere pyrolysis) is offset by its cost effectiveness. It is projected that higher yields can be obtained by using a powdered catalyst (rather than the coarse turnings used). Also, higher yields are expected if pyrolysis is conducted in presence of $H_2$ gas and a higher boiling point amine such as: tributylamine or a higher amine is used as the solvent.

Table V shows the excellent yields obtained in glass vessels.

TABLE V

$BH_4^-$ Pyrolysis in Sealed Glass with Stainless Steel Wool (6.0 gm) at Autogenous Pressure[A]

| Compound(s) Pyrolysed | Products[B] | | | | |
|---|---|---|---|---|---|
| | $B_{10}H_{10}^{2-}$ | $R_3NBH_3$ | $R_3N$ | RH | $H_2$ |
| $(C_2H_5)_4N^+BH_4^-$ (0.0345 mole) | 0.0034 (97%) | 0 | 0.0267 | 0.0280 | n.m. |
| $(C_2H_5)_4N^+BH_4^-$ (0.0050 mole) + $(CH_3)_4N^+B_3H_8^-$ (0.0150 mole) | 0.0048[C] (96%) | 0 | 0.01[d] | 0.090[d] | n.m. |

[A]150 cc sealed glass bomb filled with stainless steel wool from bottom to the necks, 185° C., 18 hours.
[B]Moles (yield based on reactant(s) charged.
[C]$B_{10}H_{10}^2$ (anion) combined predominantly with $(CH_3)_4N^+$ (cations).
[D]Mixtures of $(C_2H_5)_3N$; $C_2H_6$ and $CH_4$ were detected, but the separation of these products was not attempted.

TABLE VI

$BH_4^-$ Pyrolysis in Stainless Steel at Autogenous Pressure[A]

| Compound Pyrolyzed | $B_{10}H_{10}^{-2}$ | $R_3NBH_3^1$ | $H_2$ | $R_3N$ | RH |
|---|---|---|---|---|---|
| $(n-C_4H_9)_4N^+BH_4^-$ (.0389 moles) | 0.0038 (97.4%) | 0 | .0430 | .0308 | .0310 |
| $(C_2H_5)_4N^+BH_4^-$ (.0410 moles) | .0037 (90.2%) | 0 | .0450 | .0340 | .0340 |
| $(CH_3)_4N^+BH_4^-$ (.0580 moles) | .0037 (55.2%) | .0288 (42.7%) | .0400 | .0302 | .0590 |
| $(CH_3)_3(C_2H_5N^+BH_4^-$ (.0580 moles) | .0055 (94.50%) | .0029[C] (5.0%) | .0650 | .0462[C] | .0460 [C] |
| $(CH_3)_3(nC_4H_9)N^+BH_4^-$ (.0458 moles) | .0033 (71.7%) | .0123 (26.9%) | .0370 | .0265 | .0390 |
| $(CH_3)_3(s-C_4H_9)N^+BH_4^-$ (.0481 moles) | .0037 (77.1%) | .0096 (20.0%) | .0420 | .0302 | .0400 |
| $(CH_3)_3(t-C_4H_9)N^+BH_4^-$ (.0458 moles) | .0040 (87.0%) | .0049 (10.6%) | .0440 | .0310 | .0322 |

[A]150 cc stainless steel bomb, 185° C., 18 hours.
[B]Moles (yield based on $BH_4^-$ charged).
[C]Predominantely $(CH_3)_3N$, $(CH_3)_3NBH_3$, and ethane. Trace of $CH_4,C_2H_5(CH_3)_2N$, and $C_2H_5(CH_3)_2NBH_3$ were detected when stainless steel catalyst is used under autogenous pressure.

Comparison in Table VI of the n-butyl; sec-butyl- and tert-butyltrimethyl-ammonium borohydrides is of interest. Yields increase from 72% for the n-butyl- to 77% for sec-butyl- to 87% for the t-butyl-, indicating that increased branching favors higher yields. Methyl groups are least favorable, with tetramethylammonium-borohydride giving only 55% yield. Although they were not studied carefully, there is a parallel with yields in the minimum temperature for observable reaction - the higher yield, the lower minimum pyrolysis temperature.

This pyrolysis is similar to the Hofmann degradation of quaternary ammonium hydroxides, a very old reaction which played an important part in structure determination during the development of the chemistry of organic nitrogen compounds. In the Hofmann reaction, longer and more branched alkyl groups are lost in higher yield and at lower temperatures than smaller groups. The alkyl moieties appear as product alkenes in the Hofmann degradation. The Hofmann reaction is considered to proceed by a beta-elimination mechanism in which protons (at the carbon which is one carbon removed from the positive nitrogen) are abstracted by hydroxide ion, resulting in neutral amine/alkene and water as products. Methyl and other groups without beta-hydrogens are slow to pyrolyze, but do appear at slightly elevated temperatures as the corresponding alcohols. The fact that alkanes are observed in all cases (beta-hydrogen or no), suggests that perhaps the reaction goes by a mechanism involving hydride attack at the α-carbon. It seems possible that the Hofmann reaction goes by a similar process, but the resulting alcohols dehydrate to give alkenes (if beta-hydrogen is available).

Ion exchange resins useful in this invention are widely available commercially. They are composed of a matrix which is polystyrene cross-linked with 3-8% of divinylbenzene. The cation exchangers suitable for use in this invention contain sulfonic acid groups introduced by nuclear sulfonation. Exchangers of the described type are available from Rohm and Haas Co. under the trade name Amberlite resins and from the Dow Chemical Co. as Dowex resins. A publication "Dowex-Ion Exchange", Dow Chemical Company, describes products and uses for ion exchange resins available from this Company. The firms of Fisher and Matheson, Coleman and Bell identify other resin offered as Rexyns and as Permutits, respectively. The publication: "Reagents for Organic Synthesis", by Louis Fieser and Mary Fieser, describes ion exchange resins along with examples of uses of these resins.

The Chemist's Companion, a Handbook of Practical Data, Techniques and References, by Arnold J. Gordon and Richard A. Ford, provides a table of common resins including Dowex 50-X8 which are employed in the examples of this invention. The knowledge of the same active group on an exchange resin made available by many manufacturers enables one to select resins which can be used interchangeably, although they are not necessarily identical in composition or physical properties. For example, the cation exchange resins which are strongly acidic can be of the phenolic type (e.g., Ar-$CH_2SO_3^-H^+$) (Ar=aryl) and polystyrene type (Ph-$SO_3^-H^+$) (Ph=phenyl). The cation exchange resins are readily converted to a type in accordance with the needs of the user. The resin once placed in an exchange column can be eluted with an appropriate solvent or eluting agent to restore the usefulness or modify the resin to a more useful type in accordance with the needs of the user.

Dowex 50-X8, selected for use in accordance with this invention, is a sulfonic acid salt of styrene-divinyl-benzene copolymer ($Na^+$ salt), about 92% styrene crosslinked with about 8% divinylbenzene. It is strongly acidic, and it will function over the complete pH range (from 1 to 14), and up to 150° C. operating temperature. Its bead size is 20-50 mesh.

Other ion exchange procedures related to this invention were examined including the use of an anion exchange resin. Attempts to exchange $BH_4^-$ for $I^-$ by treating borohydride-form anion exchange resins with quaternary ammonium iodides were not very successful. Apparently the long times needed resulted in considerable decomposition of the borohydride ion. Pure water proved to be an inadequate medium for ion exchange despite its favorable solubility properties—the decomposition of $BH_4^-$ is far more pronounced in pure water and evaporation was slow. Methanol produced very rapid destruction of $BH_4^-$; ethanol was less destructive than pure water but still produced significant loss of $BH_4^-$.

The precursor compound for producing dilithiodecaborane-10 is characterized as having the formula $(R_4N)_2B_{10}H_{10}$ wherein R equals $C_nH_{2n+1}$ and n equals 2, 3, or 4. The dilithiodecaborane-10 is the precursor for producing bis(dimethyl sulfide)decaborane-12 which is a precursor compound when reacted with propargyl propionate yields carboranylmethyl propionate. The precursor compound when reacted with 1-octyne yields n-hexylcarborane. The precursor compound when reacted with propargylethyl sulfide yields carboranylmethyl ethyl sulfide. The precursor compound when reacted with propargylpropyl sulfide yields carboranylmethyl propyl sulfide. Thus, the carboranyl burning rate accelerators produced from the precursor compound that was earlier produced by the disclosed reactions is an acceptable verification of the precursor compound's structure or formula.

I claim:

1. A method for preparation of a precursor compound of the formula $B_{10}H_{12}[(CH_3)_2S]_2$ comprising:

(A) completing the following steps (i)–(v) to effect the conversion of a selected compound of the formula $(R_4N)_2B_{10}H_{10}$, wherein R equals an alkyl of the formula $C_nH_{2n+1}$ and n equals 2, 3, or 4, to dilithiodecaborane-10 by:

(i) preparing a cation exchange resin column which comprises placing a glass wool plug at the bottom of a measuring burette of about 250 milliliter capacity, filling said column with water and then filling said column with a predetermined quantity of a cation exchange resin which is a sulfonic acid $-Na^+$ salt of a styrene - divinylbenzene copolymer composed of about 92% styrene that is crosslinked with about 8% divinylbenzene, said predetermined quantity of said cation exchange resin being added gradually to the top of said column in a packing operation and said water being withdrawn from the bottom of said column as said cation exchange resin is added;

(ii) converting said cation exchange resin to the $Li^+$ form by passing through said column a water solution containing about 15 grams of LiCl per 100 milliliters of water, followed by plain water rinsing of said column until $Ag^+$ no longer gives a AgCl precipitate;

(iii) dissolving up to about 30 grams of said selected compound of the formula $(R_4N)_2B_{10}H_{10}$ in water and passing said water solution of said compound through said column at a rate of about 1 milliliter per minute to form dilithiodecaborane-10, $Li_2B_{10}H_{10}$;

(iv) eluting said $Li_2B_{10}H_{10}$ with water until testing of effluent drops with $Ag^+$ shows no $B_{10}H_{10}^{-2}$ ion as evidenced by not forming a yellow-white solid;

(v) concentrating the eluted $Li_2B_{10}H_{10}$, and finally drying said $Li_2B_{10}H_{10}$ at 100° C. under a good vacuum of less than about 0.05 mm mercury to recover dehydrated $Li_2B_{10}H_{10}$; and (B) completing the following steps (vi)–(x) to effect synthesis of said precursor of the formula $B_{10}H_{12}[(CH_3)_2S]_2$ by:

(vi) placing a predetermined quantity of freshly dehydrated $Li_2B_{10}H_{10}$ in a reaction container that is provided with a means for cooling, means for stirring, and means for purging with dry $N_2$ gas, said reaction container purged with dry $N_2$ gas prior to placing said predetermined quantity of freshly dehydrated $Li_2B_{10}H_{10}$;

(vii) reducing the dry $N_2$ gas purge rate to just maintain a positive $N_2$ pressure and adding a predetermined quantity of $(CH_3)_2S$ to said reaction container;

(viii) bubbling a stream of dry HCl into said $(CH_3)_2S$ with said means for stirring or, until the solid $Li_2B_{10}H_{10}$ is dissolved;

(ix) connecting the reaction container to a source of vacuum to effect removal of volatiles; and thereafter, (x) recovering said precursor compound formed by recrystallizing said precursor compound of the formula $B_{10}H_{12}[(CH_3)_2S]_2$ by dilution with pentane which contains a solvent selected from dimethyl sulfide and benzene, said solvent comprising an amount from about 5 to about 10 percent by volume of the total diluted phase.

2. The method of claim 1 wherein predetermined quantity of said freshly dehydrated $Li_2B_{10}H_{10}$ placed in said reaction container is about 1 gram and wherein said predetermined quantity of $(CH_3)_2S$ added to said reaction container is about 15 milliliters.

* * * * *